(12) United States Patent
Van Liere (10) Patent No.: US 12,181,091 B2
(45) Date of Patent: Dec. 31, 2024

(54) LOCKABLE EXCHANGEABLE FLUID CONNECTOR AND METHOD

(71) Applicant: Bard Peripheral Vascular, Inc., Franklin Lakes, NJ (US)

(72) Inventor: Chad C. Van Liere, Phoenix, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 87 days.

(21) Appl. No.: 17/926,051

(22) PCT Filed: Jun. 15, 2020

(86) PCT No.: PCT/US2020/037735
§ 371 (c)(1),
(2) Date: Nov. 17, 2022

(87) PCT Pub. No.: WO2021/257054
PCT Pub. Date: Dec. 23, 2021

(65) Prior Publication Data
US 2023/0184362 A1     Jun. 15, 2023

(51) Int. Cl.
*F16L 37/20* (2006.01)
*A61M 39/02* (2006.01)
*A61M 39/10* (2006.01)
*F16L 37/56* (2006.01)

(52) U.S. Cl.
CPC ......... *F16L 37/20* (2013.01); *A61M 39/0208* (2013.01); *A61M 39/1011* (2013.01); *F16L 37/56* (2013.01)

(58) Field of Classification Search
CPC ....... F16L 37/20; F16L 37/56; A61M 39/1011
See application file for complete search history.

(56) References Cited

U.S. PATENT DOCUMENTS

| | | | |
|---|---|---|---|
| 5,005,876 A | * | 4/1991 | Fahl .................. F16L 37/20 |
| 5,279,597 A | | 1/1994 | Dassa et al. |
| 5,505,714 A | | 4/1996 | Dassa et al. |
| 5,562,618 A | | 10/1996 | Cai et al. |
| 5,904,380 A | * | 5/1999 | Lee .................. F16L 37/18 |

(Continued)

FOREIGN PATENT DOCUMENTS

| | | |
|---|---|---|
| EP | 2837403 B1 | 9/2016 |
| JP | 2014155625 A | 8/2014 |
| WO | 2019096864 A1 | 5/2019 |

OTHER PUBLICATIONS

PCT/US2020/037735 filed Jun. 15, 2020 International Search Report and Written Opinion dated Mar. 9, 2021.

*Primary Examiner* — Zachary T Dragicevich
(74) *Attorney, Agent, or Firm* — Rutan & Tucker LLP (57) ABSTRACT

A fluid connector system configured to couple a first fluid line structure, e.g. port, with a second fluid line structure, e.g. catheter. The connector system can include a connector body and one or more locking mechanisms designed to transition between an unlocked position and a locked position. The locking mechanism includes a first lever arm rotatably coupled to the connector body, and a second lever arm rotatably coupled to the first lever arm. The second lever arm can further be rotatably and releasably coupled to the port. Rotating the first lever arm uses mechanical advantage to urge the port to engage a catheter ensuring a tight seal therebetween even under high fluid pressures.

20 Claims, 11 Drawing Sheets

(56) References Cited

U.S. PATENT DOCUMENTS

| | | | | |
|---|---|---|---|---|
| 6,053,540 | A * | 4/2000 | Meyer | F16L 37/18 |
| 6,090,190 | A * | 7/2000 | Enhsen | B01D 15/08 |
| 6,447,016 | B2 * | 9/2002 | Collier | F16L 37/18 |
| 6,676,652 | B2 | 1/2004 | Mogg | |
| 8,142,417 | B2 | 3/2012 | Pajunk et al. | |
| 9,732,894 | B1 * | 8/2017 | Hartman | F16L 37/20 |
| 10,471,247 | B2 | 11/2019 | Kellner et al. | |
| 2008/0033350 | A1 | 2/2008 | Wilson et al. | |
| 2008/0208159 | A1 | 8/2008 | Stanus et al. | |
| 2018/0085553 | A1 | 3/2018 | Shorey | |
| 2020/0046941 | A1 | 2/2020 | Graham et al. | |

* cited by examiner

LOCKABLE EXCHANGEABLE FLUID CONNECTOR AND METHOD

PRIORITY

This application is a U.S. national stage application of International Application No. PCT/US2020/037735, filed Jun. 15, 2020, which is incorporated by reference in its entirety into this application.

SUMMARY

Embodiments disclosed herein are directed to lockable, exchangeable fluid connector systems and associated methods thereof. The connector system can include a connector body, configured to engage a catheter or similar fluid line structure, and one or more locking mechanisms designed to transition between an unlocked position and a locked position. The locking mechanism includes a first lever arm having a first end rotatably coupled to the connector body, and a second end opposite the first end, rotatably coupled to a second lever arm. The second lever arm can be rotatably and releasably coupled to a port or similar fluid line structure. Rotating one of the first lever arm or the second lever arm employs mechanical advantage to urge the port to engage the catheter ensuring a tight seal therebetween even under high fluid pressures.

Such fluid connector systems can be used in a variety of situations. For example, implantable dialysis port and catheter systems require periodic replacing. However, the functional life of the catheter, or sheath, tends to be shorter than the functional life of the port and as such, the catheter requires replacing while the port is still functional. Since the footprint of the port tends to be relatively large, ideally the catheter could be exchanged while the port remains in situ. Even if the port still needs to be removed in order to exchange the catheter, being able to reuse the port can reduce overall costs.

What is needed therefore, is a fluid connector that allows a first fluid line connector, e.g. a port, to be coupled and uncoupled to/from a second fluid line connector, e.g. a catheter, while maintaining the integrity of the connection even under high fluid pressure. The connector can be easily and repeatably locked and unlocked while one of the port or catheter remains in situ.

Disclosed herein is a fluid connector system including, a connector body and a locking mechanism coupled to the connector body and designed to transition between an unlocked position and a locked position, the locking mechanism including, a first lever arm rotatably coupled to the connector body, and a second lever arm rotatably coupled to the first lever arm, wherein the first lever arm and the second lever arm are oblique to a longitudinal axis of the connector body in the unlocked position, and parallel to the longitudinal axis of the connector body in the locked position.

In some embodiments, the connector body is coupled to a catheter, the connector body configured to engage an access port to place one or more lumens of the access port into fluid communication with one or more lumens of the catheter. The first lever arm comprises a first securement aperture, and wherein the second lever arm includes a second securement aperture. In some embodiments, the fluid connector system further includes a securement arm rotatably coupled to the second lever arm, wherein the securement arm includes a protrusion configured to extend through the first securement aperture and the second securement aperture to place the locking mechanism in the locked position. The connector body includes a protrusion configured to extend through the first securement aperture and the second securement aperture to place the locking mechanism in the locked position.

In some embodiments, the protrusion engages one of the first securement aperture or the second securement aperture with one of an interference fit, press-fit, or snap-fit engagement. A first end of the second lever arm is releaseably and rotatably coupled to the access port. A first end of the securement arm is configured to releasably and rotatably secure a first end of the second lever arm to the access port. The access port further includes a socket configured to releasably and rotatably secure one of the first end of the second lever arm or the first end of the securement arm. The socket includes one of an interference fit, press-fit, or snap-fit engagement. A first end of the first lever arm, coupled to the connector body, is disposed along a longitudinal axis, between the first end and a second end of the second lever arm in the locked position.

Also disclosed is a method of fluidly connecting an access port with a catheter including, providing a connector body coupled to the catheter, the connector body having a locking mechanism including a first lever arm rotatably coupled to the connector body, and a second lever arm rotatably coupled to the first lever arm, coupling a first end of the second lever arm to the access port, and transitioning the first lever arm from an unlocked position to a locked position, wherein the first lever arm and the second lever arm are oblique to a longitudinal axis of the connector body in the unlocked position, and parallel to the longitudinal axis of the connector body in the locked position.

In some embodiments, the connector body is configured to engage the access port to place one or more lumens of the access port into fluid communication with one or more lumens of the catheter. In some embodiments, the method further includes extending a protrusion through a first securement aperture disposed on the first lever arm and a second securement aperture disposed on the second lever arm to place the locking mechanism in the locked position. In some embodiments, the method further includes a securement arm rotatably coupled to the second lever arm, and wherein the protrusion extends laterally inward from the securement arm. The protrusion is disposed on the connector body and the protrusion extends laterally outward.

In some embodiments, the protrusion engages one of the first securement aperture or the second securement aperture with one of an interference fit, press-fit, or snap-fit engagement. A first end of the second lever arm is releaseably and rotatably coupled to the access port with one of an interference fit, press-fit, or snap-fit engagement. A first end of the securement arm is configured to releasably and rotatably couple the first end of the second lever arm to the access port. The access port further includes a socket configured to releasably and rotatably couple the first end of the second lever arm to the access port. Transitioning the first lever arm from an unlocked position to a locked position further includes disposing a first end of the first lever arm, coupled to the connector body, along a longitudinal axis between the first end and a second end of the second lever arm.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Figure 1A:
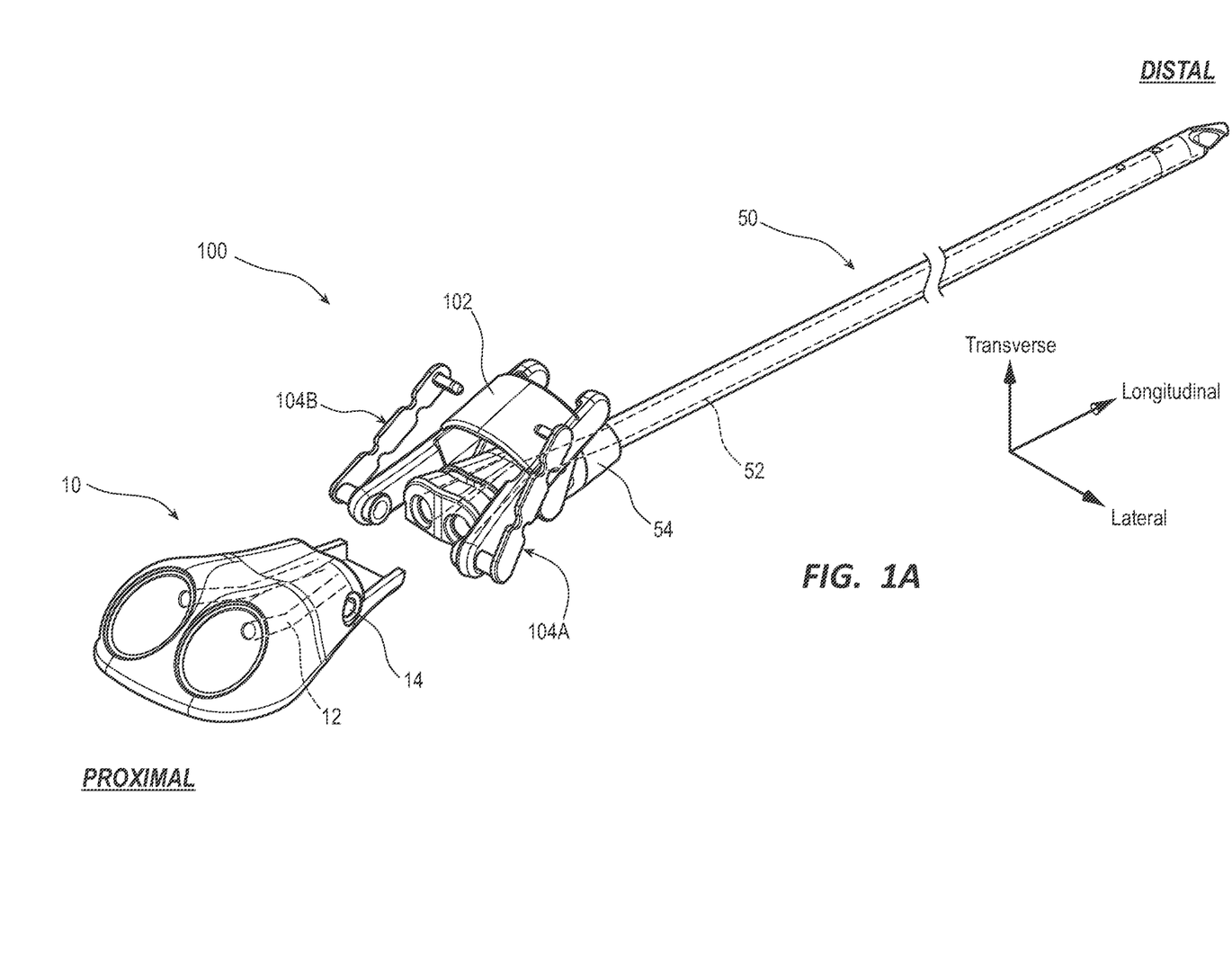
FIG. 1A shows a perspective view of an exemplary fluid connector system in an unlocked configuration, in accordance with embodiments disclosed herein.

As shown in FIG. 1A, and to assist in the description of embodiments described herein, a longitudinal axis extends substantially parallel to an axial length of the catheter. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

Figure 1B:
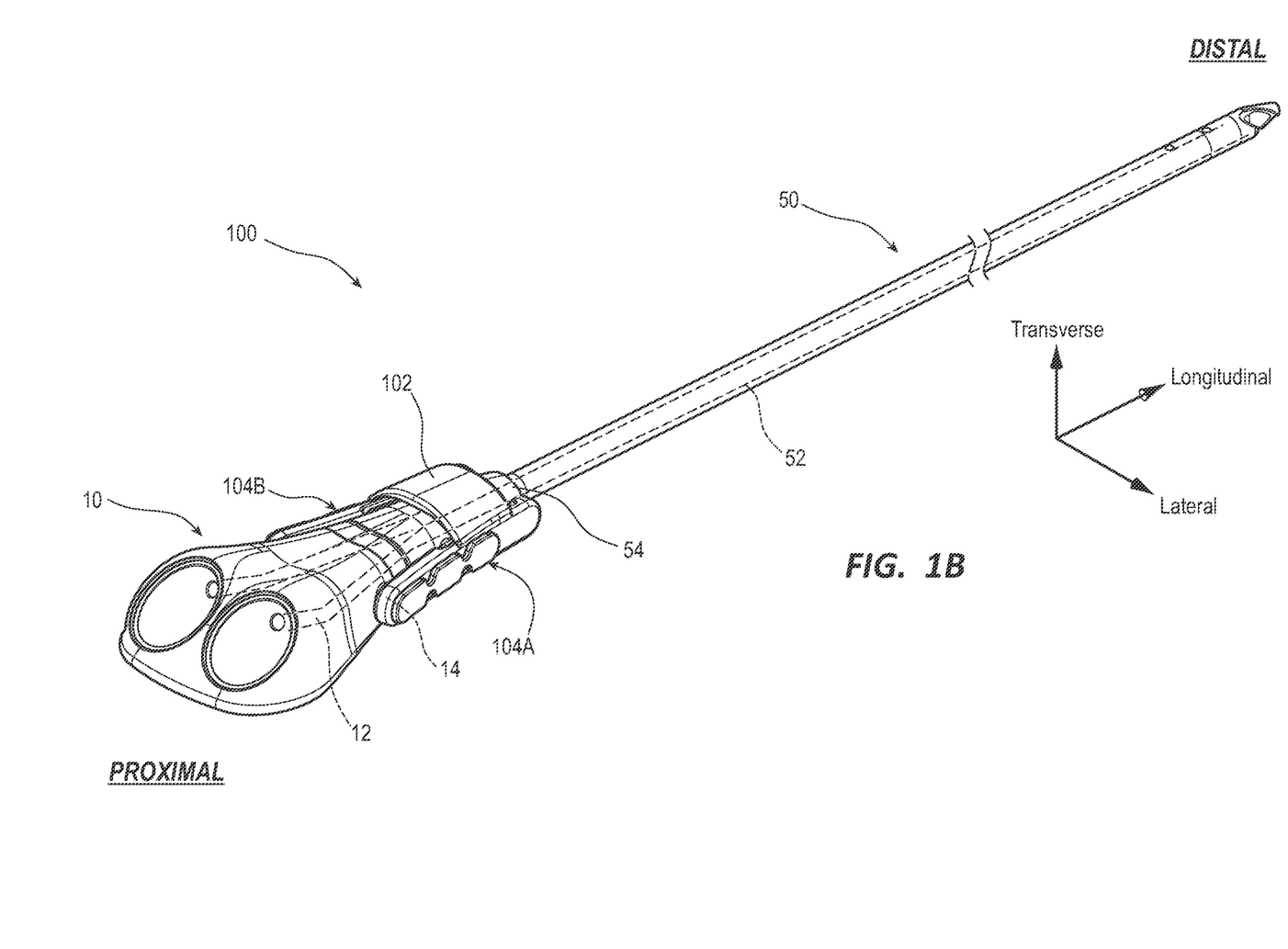
FIG. 1B shows a perspective view of an exemplary fluid connector system in a locked configuration, in accordance with embodiments disclosed herein.
Figure 1C:
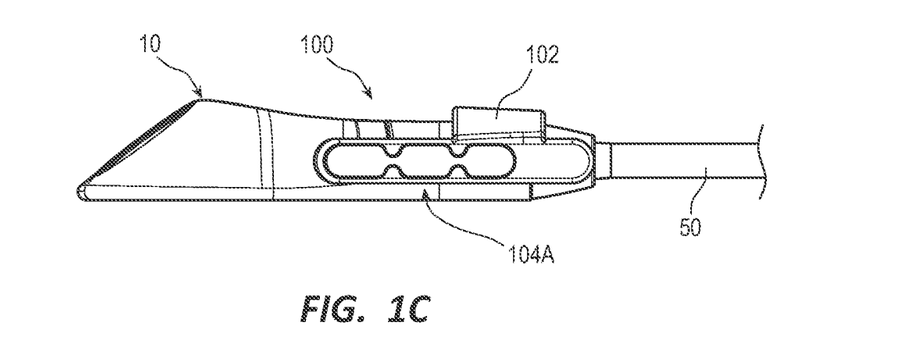
FIG. 1C shows a side view of an exemplary fluid connector system in a locked configuration, in accordance with embodiments disclosed herein.
Figure 1D:
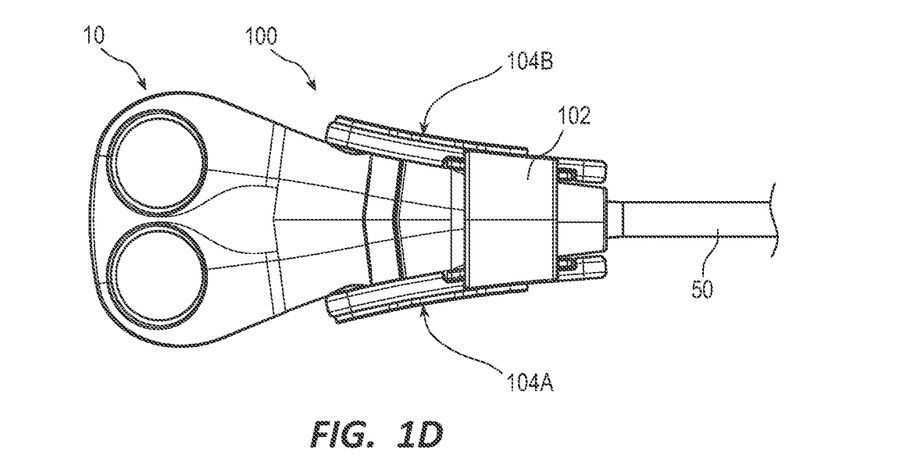
FIG. 1D shows a plan view of an exemplary fluid connector system in a locked configuration, in accordance with embodiments disclosed herein.
Figure 1E:
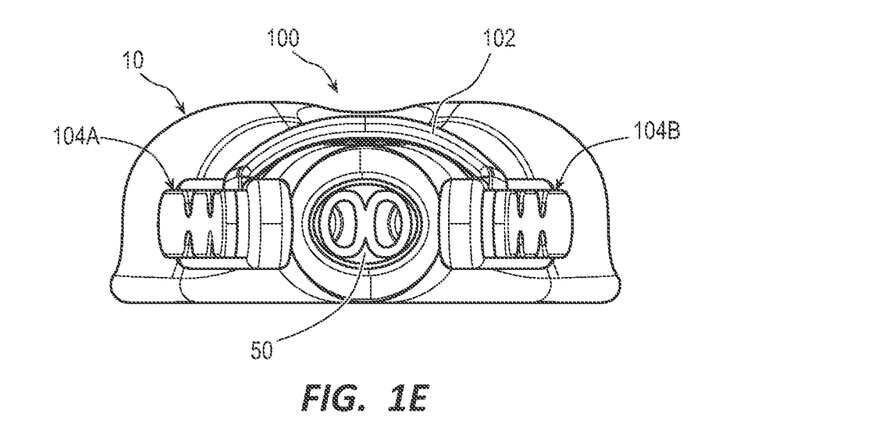
FIG. 1E shows an end view of an exemplary fluid connector system in a locked configuration, in accordance with embodiments disclosed herein.

The present disclosure relates generally to lockable, exchangeable, fluid connector systems and methods thereof. FIGS. 1A-1B show an exemplary lockable, exchangeable fluid connector system ("system") 100. FIG. 1A shows the system 100 in an unlocked configuration, FIG. 1B shows the system 100 in a locked configuration. In an embodiment, the system 100 can include a connector body 102 and one or more locking mechanisms 104, for example a first locking mechanism 104A and a second locking mechanism 104B.

In an embodiment, the first locking mechanism 104A can be disposed opposite a second locking mechanism 104B across a central axis, although it will be appreciated that other configurations of locking mechanism(s) 104 are considered to fall within the scope of the present invention. Further it will be appreciated that one or more locking mechanisms 104 can be oriented the same direction, different directions, in "mirror image," combinations thereof, or the like, without departing from the spirit of the invention.

In an embodiment, the locking system 100 can be configured to couple a first fluid line structure with a second fluid line structure to provide fluid communication therebetween. As used herein, the term "fluid line structure" can include a device configured to provide fluid communication and can include, but not limited to, a catheter, tube, single lumen catheter, multi-lumen catheter, dialysis catheter, central venous catheter ("CVC"), peripherally inserted central catheter (PICC), midline catheter, intravascular access port ("port"), intravenous (I.V.) fluid line, medical drainage line, medical pressurized fluid line, combinations thereof, or the like. In an embodiment, the lockable fluid connector system 100 can be provided as part of a kit including one or more fluid line structures. For example, embodiments described herein show a lockable, exchangeable fluid connector system 100 coupling a low-profile dialysis port 10 with a dual lumen catheter 50, however it will be appreciated that these are exemplary medical line structures and are not intended to be limiting in any way. In an embodiment, the connector system 10 can be provided as part of a kit including one or more of a port 10 or a catheter 50.

In general, a first medical line structure, e.g. port 10, includes one or more lumen and a second medical line structure, e.g. catheter 50, also includes one or more lumen. The system 100 can be configured to align the port lumen 12 with the catheter lumen 52 and releasably secure the port 10 with the catheter 50 to provide fluid communication therebetween. Advantageously, the system 100 can ensure a fluid tight seal between the port lumen 12 and the catheter lumen 52, even if a fluid disposed therein is under pressure. Further, as shown in FIGS. 1B-1E, in a locked configuration, the system 100 maintains a low outer profile relative to the outer profile of the medical line structures, i.e. the port 10 and the catheter 50. This can mitigate scarring when disposed subcutaneously as well as mitigate tissue ingrowth.

Figure 2A:
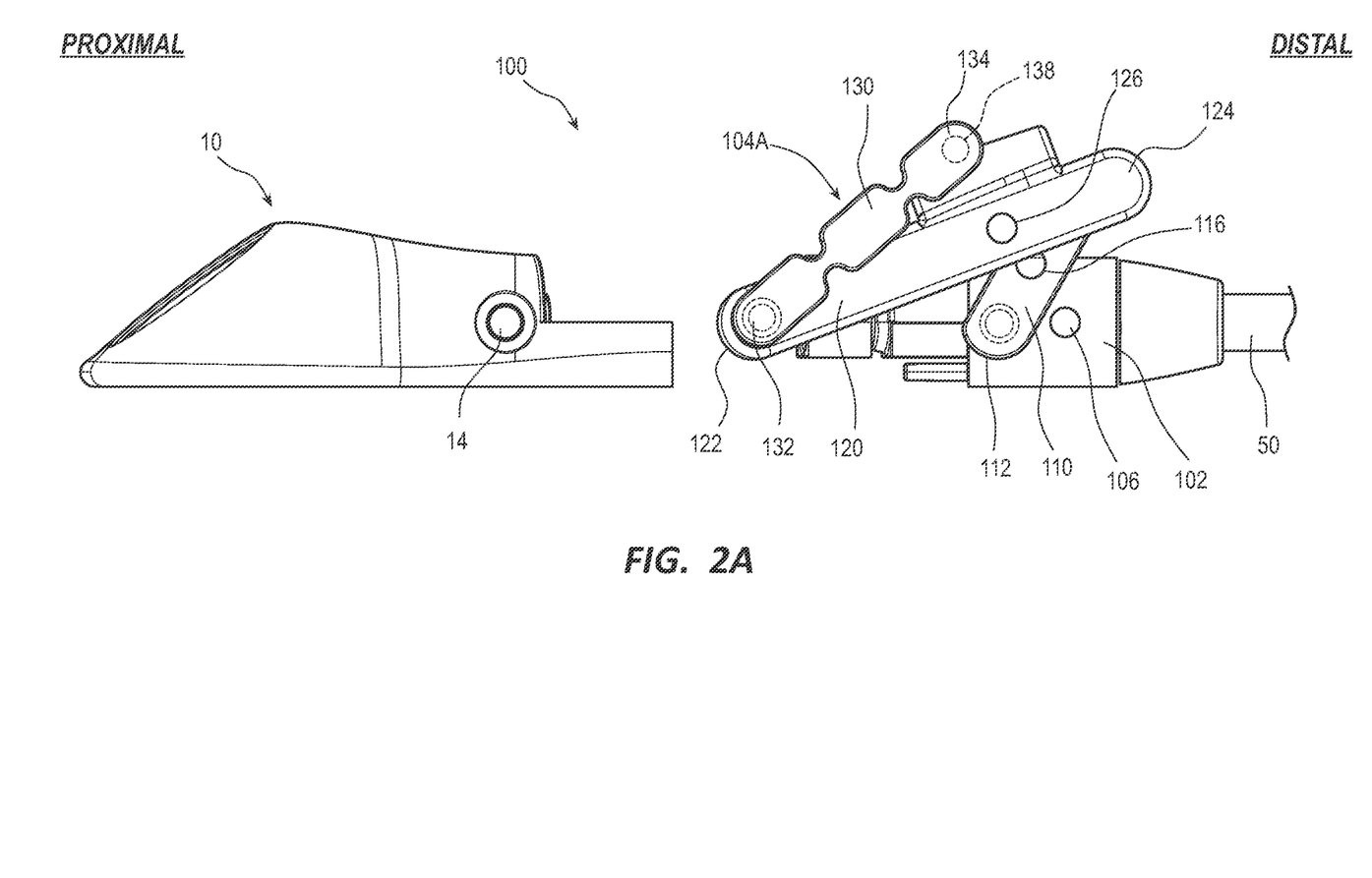
FIG. 2A shows a side view of an exemplary fluid connector system in an unlocked configuration, in accordance with embodiments disclosed herein.
Figure 2B:
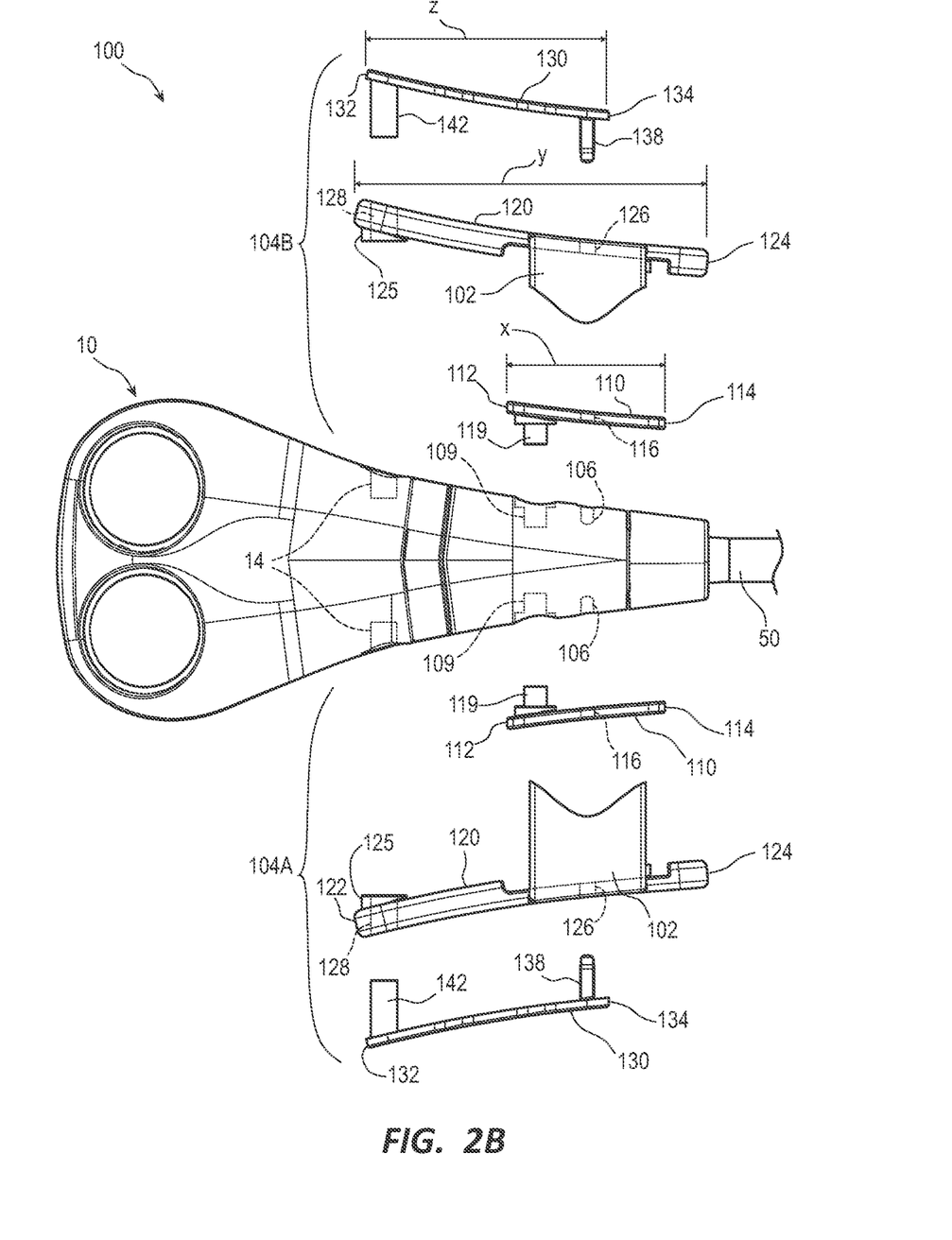
FIG. 2B shows an exploded view of an embodiment of a fluid connector system, in accordance with embodiments disclosed herein.
Figure 2C:
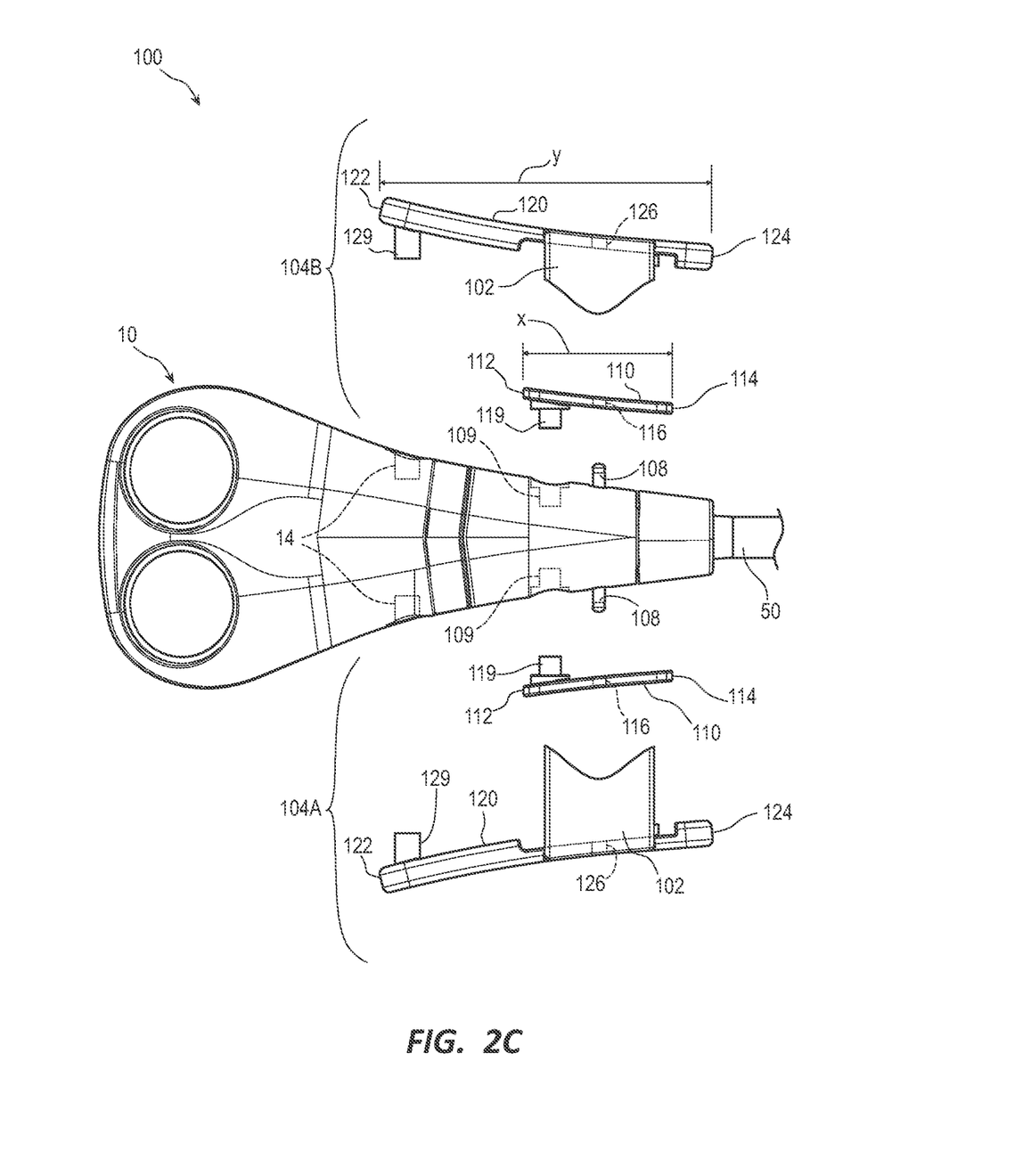
FIG. 2C shows an exploded view of an embodiment of a fluid connector system, in accordance with embodiments disclosed herein.

FIGS. 2A-2C show various embodiments of a connector system 100. FIG. 2A shows a side view of the connector system 100 in the unlocked configuration. FIGS. 2B-2C show exploded plan views of embodiments of a connector system 100. The connector system 100 can include a connector body 102. In an embodiment, the connector body 102 can be a separate structure from the catheter 50, and can be configured to be coupled thereto. For example, the connector body 102 can define a tapered lumen, extending axially and configured to receive a catheter hub 54 therein. In an embodiment, the connector body 102 can be coupled to the catheter 50 by an interference fit, press fit, snap fit engagement, the connector body 102 can be hingedly coupled to the catheter 50, or coupled thereto by bonding, welding, adhesive, combinations thereof, of the like. In an embodiment the connector body 102 is formed integrally with the catheter 50 as a single monolithic piece.

In an embodiment, a locking mechanism 104 of the system 100 can include a first lever arm 110 and a second lever arm 120. The first lever arm 110 can extend from a first end 112 to a second end 114, opposite the first end 112, to define a first lever arm length (x). The second lever arm 120 can extend from a first end 122 to a second end 124, opposite the first end 122 to define a second lever arm length (y). In an embodiment, the locking mechanism 100 further includes a securement arm 130 that extends from a first end 132 to a second end 134, opposite the first end 132, to define a securement arm length (z). In an embodiment, a first lever arm length (x) is the same, or less than, a second lever arm length (y). In an embodiment, the first lever arm length (x) is substantially half of the length (y) of the second lever arm 120. In an embodiment, the securement arm length (z) is the same, or less than, a second lever arm length (y). In an embodiment, the securement arm length (z) is the same or greater than the first lever arm length (x)

In an embodiment, as shown in FIG. 2A, in an unlocked position the first lever arm first end 112 is disposed proximally of the first lever arm second end 114. Similarly, the second lever arm first end 122 is disposed proximally of the second lever arm second end 124. In an embodiment, a first lever first end 112 can be disposed distally of a second lever first end 122. However, it will be appreciated that the locking mechanism 104 can also be oriented in an opposite direction without departing from the spirit of the invention, i.e. a first lever first end 112 disposed proximally of a second lever first end 122. In an embodiment, one of the first lever arm 110 or the second lever arm 120 can be disposed at an oblique angle, relative to the longitudinal axis, when in the unlocked position.

In an embodiment, the first lever arm 110 can be rotatably coupled to the connector body 102. For example, the first lever arm first end 112 can include pinion 119 configured to engage a socket 109 in a press fit, snap fit engagement, or the like, to rotatably couple the first lever arm 110 to the connector body 102. As used herein, the term "rotatably coupled" can include a pinion and socket, hinge, living hinge, lug and detent, press fit, snap fit engagement, or similar suitable mechanism. In an embodiment, the first lever arm 110 can be rotatably coupled to a second lever arm 120. For example, a first lever arm second end 114 can be rotatably coupled to a second lever arm second end 124.

In an embodiment, a second lever arm first end 122 can be releasably and rotatably coupled to a first medical line structure, e.g. a port 10. In an embodiment, the port 10 can include a socket 14 or similar structure configured to releasably and rotatably couple the second lever arm first end 122 to the port 10. In an embodiment, as shown in FIG. 2C, the second lever arm first end 122 can include a pinion 129 configured to engage the socket 14 in an interference fit, press fit, snap fit engagement, or similar suitable engagement.

In an embodiment, one of the first lever arm 110 or the second lever arm 120 includes a securement aperture. For example, the first lever arm 110 can include a first securement aperture 116 and the second lever arm 120 can include a second securement aperture 126. In an embodiment, as shown in FIG. 2B, the locking mechanism 104 can further include a securement arm 130. The securement arm 130 can be rotatably coupled with the second lever arm 120. For example, a first end 132 of the securement arm 130 can be rotatably coupled to a first end 122 of the second lever arm 120. The securement arm 130 can include a locking protrusion ("protrusion") 138. In a locked configuration, the locking protrusion 138 is configured to extend through one of the second securement aperture 126, the first securement aperture 116, or a securement socket 106 disposed in the connector body 102. The locking protrusion 138 secures one of the first lever arm 110 and the second lever arm 120 in a locked configuration, i.e. extending substantially parallel to a longitudinal axis with a first lever arm first end 112 disposed between the second lever arm first end 122 and the second lever arm second end 124.

In an embodiment, the securement arm 130 can be rotatably or hingedly coupled to one of the first lever arm 110, connector body 102, or catheter 50, and can be configured to engage one of the first securement aperture 116 or second securement aperture 126, as described herein, to secure the locking mechanism 104 in a locked configuration. In an embodiment, the securement arm 130 can include one or more notches 136 configured to impart flexible characteristics on the securement arm 130 to allow the locking protrusion 138 to be inserted through one of the securement apertures 116, 126.

In an embodiment, as shown in FIG. 2C, a connector body 102 includes a locking protrusion ("protrusion") 108. In a locked configuration, the locking protrusion 108 can be configured to extend through one of the first securement aperture 116, or the second securement aperture 126 and can secure one of the first lever arm 110 and the second lever arm 120 in the locked configuration, i.e. extending substantially parallel to a longitudinal axis with a first lever arm first end 112 disposed between the second lever arm first end 122 and the second lever arm second end 124.

As will be appreciated, embodiments of the connector system 100 can include one or more of the locking mechanisms 104 including a connector locking protrusion 108, a securement arm 130 and protrusion 138, or combinations thereof. In an embodiment, the locking mechanisms 104A, 104B can be the same, or different. For example a first locking mechanism can include a connector locking protrusion 108, and a second locking mechanism can include a securement arm 130 and locking protrusion 138. In an embodiment, the locking mechanisms 104A, 104B can be "mirror images" of each other. These and similar combinations are considered to fall within the scope of the present invention.

As shown in FIGS. 3A-3D, in an exemplary method of use, a locking system 100 is provided as described herein. A port 10, including a port lumen 12, can be aligned with a catheter lumen 52 of the catheter 50. In an embodiment, one of the port 10 or catheter 50 can include one or more fluid coupling structures to provide fluid communication between the port lumen 12 and the catheter lumen 52. Exemplary fluid coupling structures can include port stem, septum, valves, sockets, recesses, bushings, grommets, combinations thereof, or the like. In an embodiment, the port lumen 12 can engage the catheter lumen 52 in an interference fit, press fit, snap fit engagement, or the like.

In an embodiment, the locking system 100, including a connector body 102 and one or more locking mechanisms 104, can be coupled with one of the first medical line structure or the second medical line structure. For example, as shown, the connector body 102 is coupled with the catheter 50 and can be releasably engaged with the port 10. However, it will be appreciated that, in an embodiment, the connector body 102 can be coupled with the port 10 and can be releasably engaged with the catheter 50.

Figure 3A:
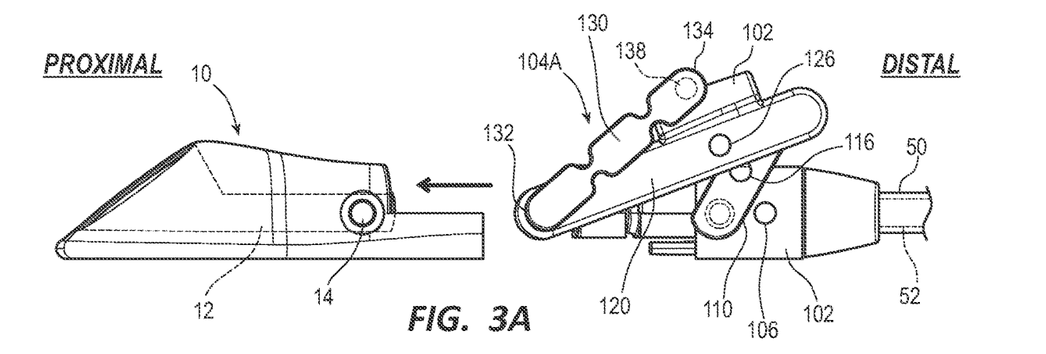
FIGS. 3A-3D show side views of a fluid connector system transitioning between an unlocked configuration and a locked configuration, in accordance with embodiments disclosed herein.
Figure 3B:
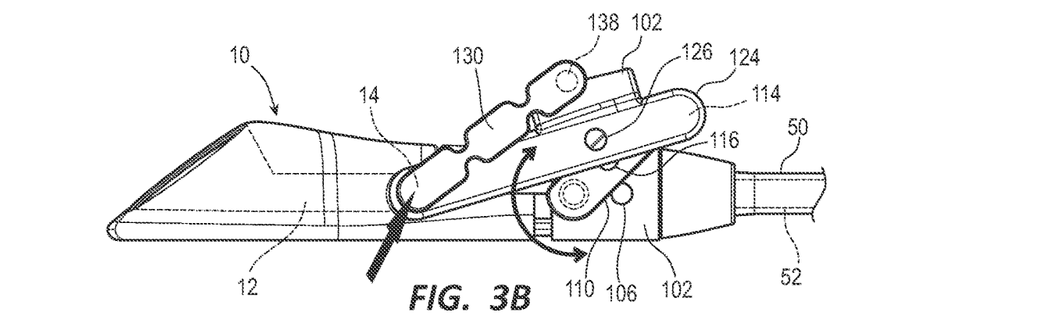

As shown in FIG. 3B, a second lever arm first end 122 can be releasably and rotatably coupled to the port 10. For example, the second lever arm first end 122 can be releasably and rotatably coupled with a socket 14, disposed on the port 10, in a snap fit engagement by urging the second lever arm first end 122 laterally inward.

Figure 3C:
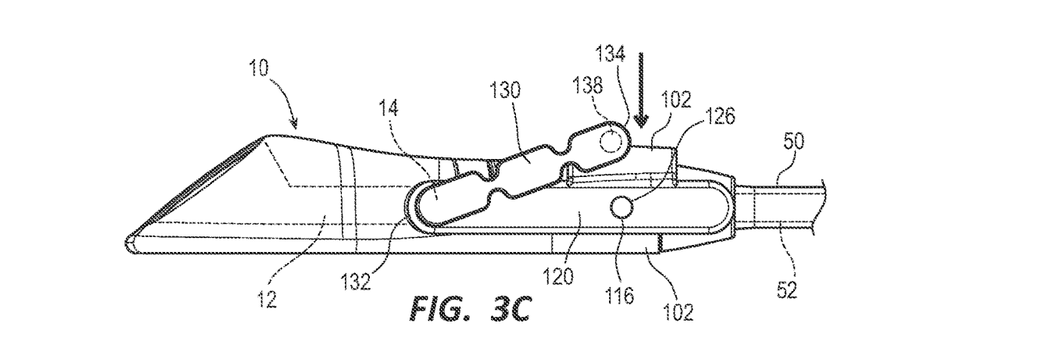

As shown in FIGS. 3B-3C, the locking mechanism 104 can be transitioned from an unlocked configuration (FIG. 3B) to a locked configuration (FIG. 3C). The first lever arm 110 can be rotated, either clockwise or anti-clockwise, until the first lever arm first end 112 is disposed between the second lever arm first end 122 and the second lever arm second end 124 along a longitudinal axis, i.e. until the first lever arm 110 and the second lever arm 120 substantially aligns with a longitudinal axis. To note, as shown in FIG. 3C, in the locked configuration, the first securement aperture 116 and the second securement aperture 126 substantially align along a lateral axis. As will be appreciated, rotating the first lever arm 110 from the unlocked position to the locked position urges the second lever arm 120, and the port 10 coupled thereto, towards the connector body 102. The interaction between the first lever arm 110 and the second lever arm 120 of the locking mechanism provides a mechanical advantage such that a force applied by the locking mechanism to urge the port 10 towards the catheter 50 is greater than a force required to transition the locking mechanism 104 from the unlocked position to the locked.

Figure 3D:
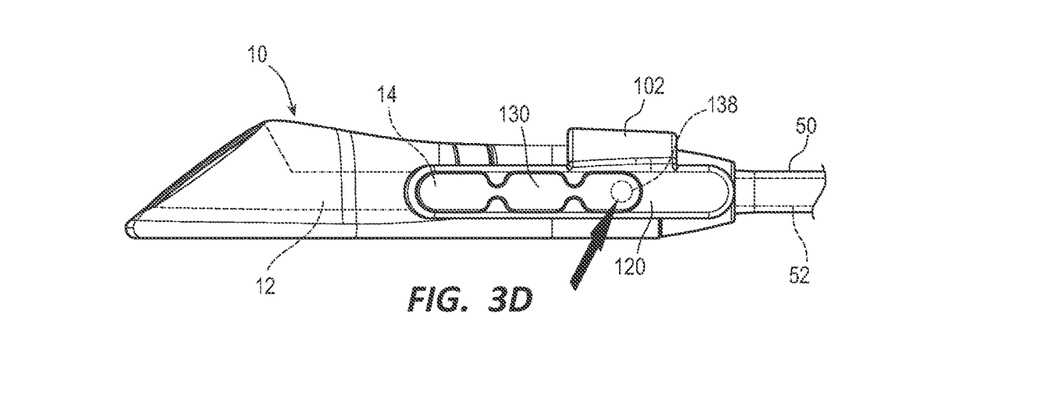

In an embodiment, a securement protrusion, e.g. a connector securement protrusion 108 or a securement arm securement protrusion 138, can be disposed through one of the first securement aperture 116 or the second securement aperture 126 to secure the locking mechanism 104 in the locked position. As shown in FIGS. 3C-3D, the protrusion 138 can engage the securement apertures 116, 126 and the securement socket 106, in either an interference fit, press fit, snap fit engagement, or the like.

For example, in an embodiment, a securement arm 130 can be rotatably coupled to the second lever arm 120. i.e. A securement arm first end 132 can be rotatably coupled to the second lever arm first end 122. A securement protrusion 138 can be disposed at a second end 134 of the securement arm 130 and extend laterally inward. The securement arm 130 can be rotated through a longitudinally vertical plane until the protrusion 138 aligns with one of the second securement aperture 126, the first securement aperture 116, or a securement socket 106 disposed on the connector body 102. The securement arm second end 134 can then be urged laterally inward such that the protrusion 138 engages one of the second securement aperture 126, the first securement aperture 116, or securement socket 106 to secure the locking mechanism in the locked configuration.

In an embodiment, a connector body protrusion 108 can be disposed on the connector body 102 and extend laterally outward. When one of the first lever 110 or the second lever 120 are in the locked configuration, the protrusion 108 can align with one of the first securement aperture 116 or the second securement aperture 126. One of the first lever second end 114 or the second lever second end 124 can then be urged laterally inward so that the protrusion engages one of the first securement aperture 116 or the second securement aperture 126 to maintain the locking mechanism 104 in the locked configuration.

In an embodiment, the locking mechanism 104 can include both a connector body protrusion 108 and a securement arm 130 including a securement arm protrusion 138. One of the connector body protrusion 108 and the securement arm protrusion 138 can engage one of the first securement aperture 116 and the second securement aperture 126 to maintain the locking mechanism 104 in the locked configuration.

In an embodiment, to disengage the port 10 from the catheter 50, when the locking mechanism 104 is in the locked configuration, the process can be reversed. In an embodiment, the securement arm protrusion 138 can be urged laterally outward to disengage the securement arm protrusion 138 from one of the first securement aperture 116 or the second securement aperture 126. In an embodiment, one of the first lever arm second end 114 or the second lever arm second end 124 can be urged laterally outward to disengage one of the first securement aperture 116 or the second securement aperture 126 from the connector body protrusion 108.

The first lever arm 110 can then be rotated, either clockwise or anti-clockwise. The mechanical advantage of the first lever arm 110 and the second lever arm 120 can urge the port 10 longitudinally away from the catheter 50, disengaging the port lumen 12 from the catheter lumen 52. The second lever arm first end 122 can then urged laterally outward to detach from the socket 14 to release the port 10 therefrom.

Figure 4A:
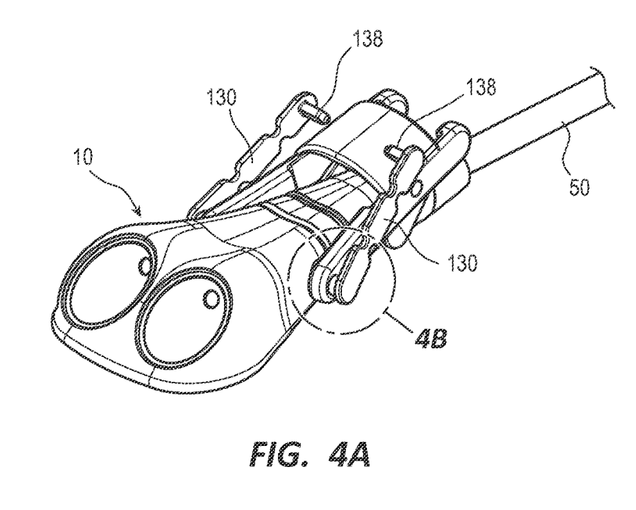
FIG. 4A shows a perspective view of a fluid connector system, in accordance with embodiments disclosed herein.
Figure 4B:
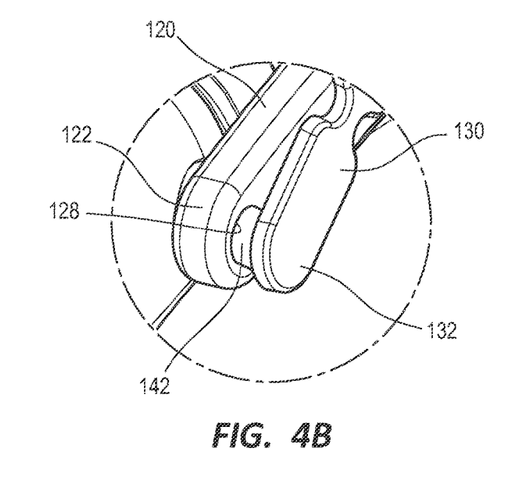
FIG. 4B shows close up detail of the fluid connector system shown in FIG. 4A, in accordance with embodiments disclosed herein.
Figure 4C:
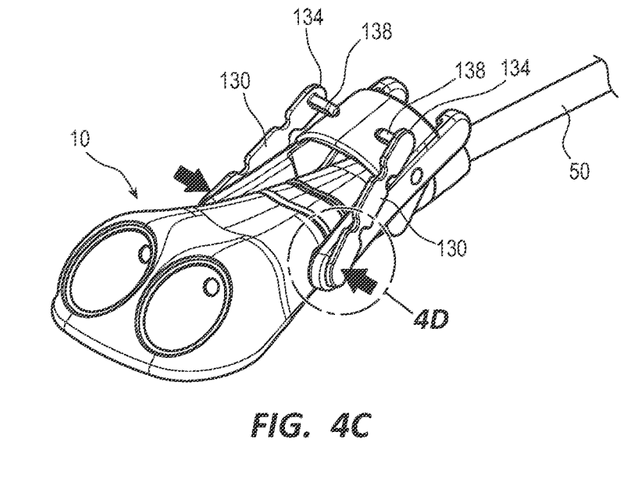
FIG. 4C shows a perspective view of a fluid connector system, in accordance with embodiments disclosed herein.
Figure 4D:
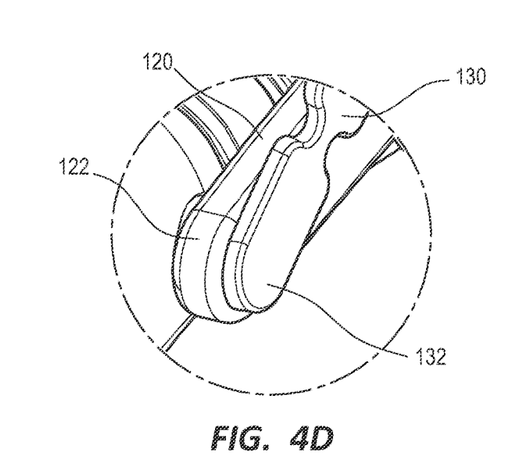
FIG. 4D shows close up detail of the fluid connector system shown in FIG. 4C, in accordance with embodiments disclosed herein.

As shown in FIGS. 4A-4D, in an embodiment, a securement arm first end 132 can be configured to engage the socket 14 to rotatably and releasably secure a second lever arm first end 122 to the port 10. As shown in FIGS. 2B, 4B, the second lever arm first end 122 can include a coupling aperture 128 and the securement arm first end 132 can include a coupling pinion 142. The coupling pinion 142 can extend through the coupling aperture 128 and releaseably and rotatably engage the socket 14 disposed on the port 10. The coupling pinion 142 can engage the socket 14 in an interference fit, press fit, or snap fit engagement, or the like, by urging the securement arm first end 132 laterally inward, as shown in FIGS. 4C-4D. In like manner the coupling pinion 142 releasably and rotatably secures the second lever arm first end 122 to the port 10.

Figure 5A:
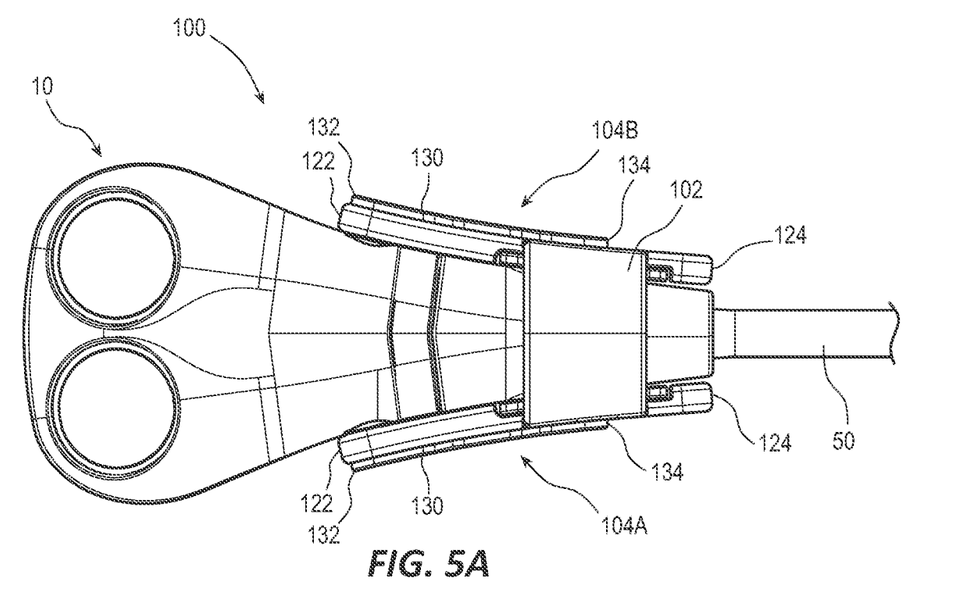
FIG. 5A shows a plan view of a fluid connector system in a locked configuration, in accordance with embodiments disclosed herein.
Figure 5B:
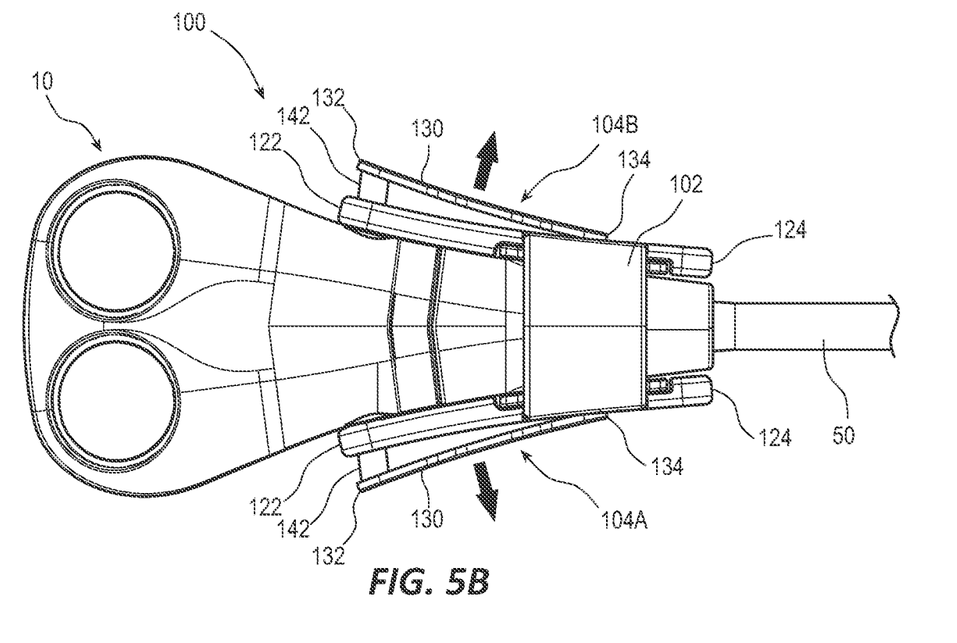
FIG. 5B shows a plan view of a fluid connector system in an unlocked configuration, in accordance with embodiments disclosed herein.

In an embodiment, to disengage the port 10 from the catheter 50, as shown in FIGS. 5A-5B, the securement arm first end 132 can be urged laterally outward to disengage the coupling pinion 142 from the socket 14 and disengage the port 10 from the locking mechanism 104. The port 10 can then be urged longitudinally away from the catheter 50 while the locking mechanism 104 remains in the locked configuration. Advantageously, this provides fewer steps, reducing the time required for explantation.

Figure 5C:
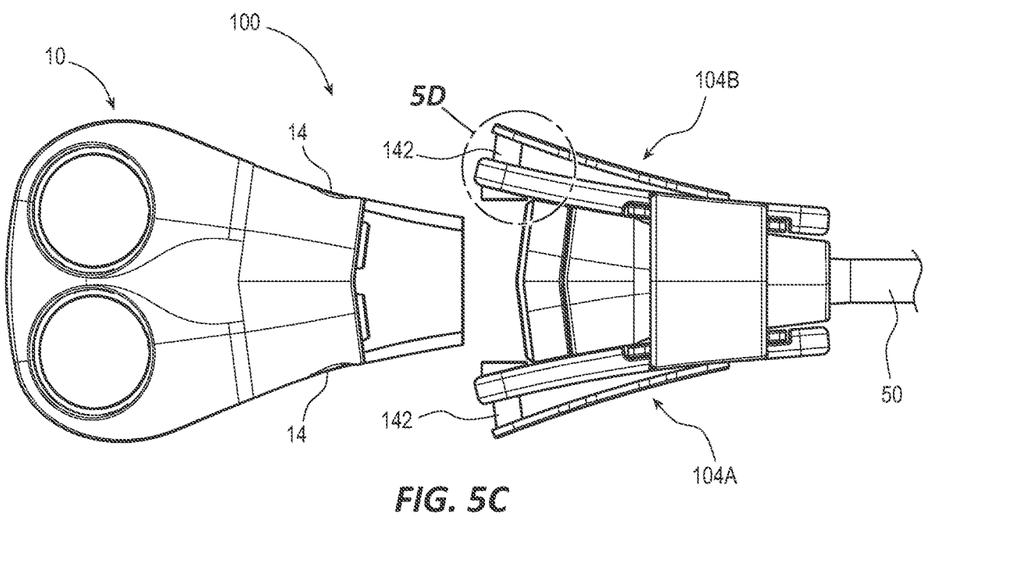
FIG. 5C shows a plan view of a fluid connector system, in accordance with embodiments disclosed herein.
Figure 5D:
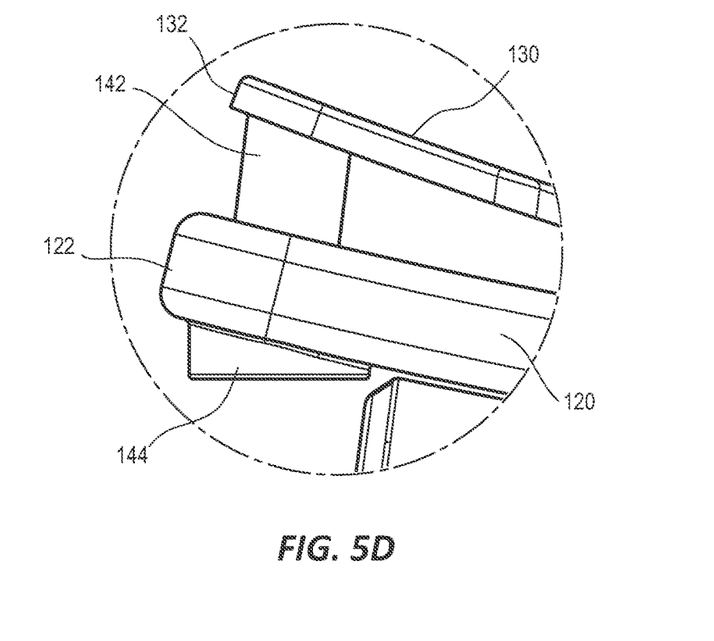
FIG. 5D shows close up detail of the fluid connector system shown in FIG. 5C, in accordance with embodiments disclosed herein.
Figure 5E:
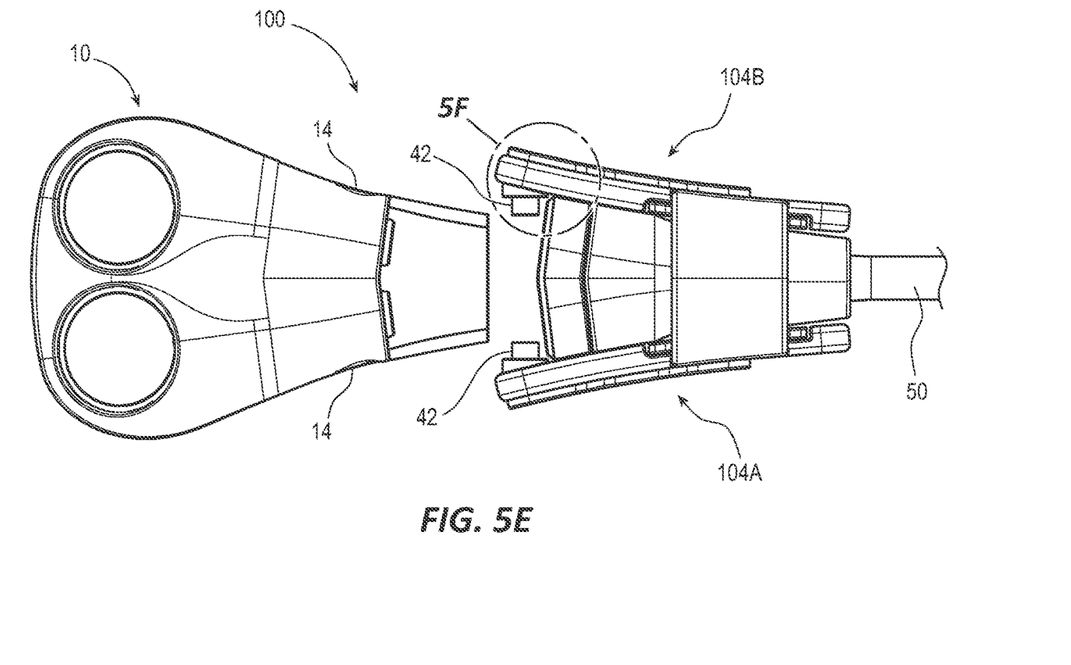
FIG. 5E shows a plan view of a fluid connector system, in accordance with embodiments disclosed herein.
Figure 5F:
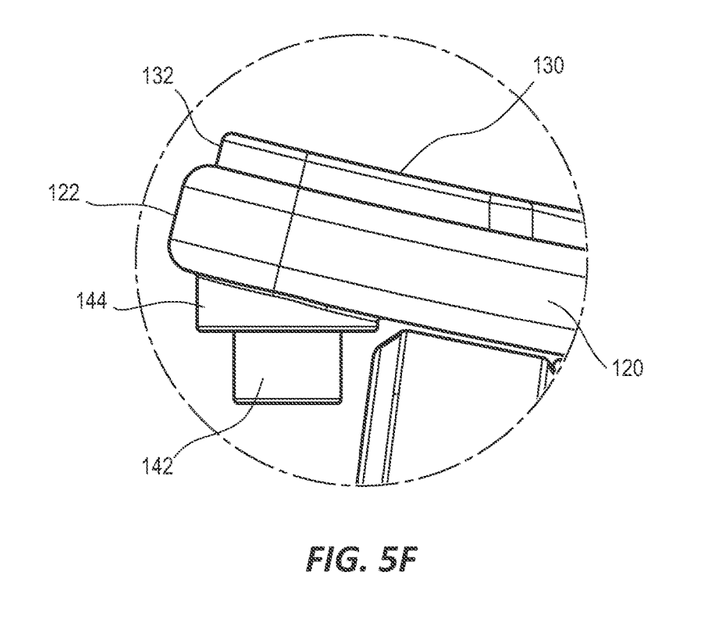
FIG. 5F shows close up detail of the fluid connector system shown in FIG. 5E, in accordance with embodiments disclosed herein.

For clarity, FIGS. 5C-5D show the coupling pinion 142 transitioning between a disengaged position (FIG. 5C-5D) and an engaged position (FIG. 5E-5F), as described above, with the port 10 removed to illustrate the lateral movement of the coupling pinions 142. Optionally, the coupling aperture 128 may include a bushing 144 or similar structure rotatably or pivotally disposed therein and configured to align an axis of the coupling aperture 128 with an axis of the socket 14 to facilitate engagement between the coupling pinion 142 and the socket 14.

Advantageously, embodiments of the connector system 100 described herein provide a self-contained activation and locking mechanism. A port 10 can be coupled to, or explanted from, the catheter 50 without requiring adhesive, sutures, screws, kit tools, or the like. Further, the mechanical advantage of the locking mechanism 104 can compress a sealing septum, or similar fluid coupling structures, to ensure a fluid tight seal between the port lumen 12 and the catheter lumen 52. The amount of force required by the user to lock the locking mechanism can be the same or less than the amount of force applied by the locking mechanism to ensure a fluid tight seal. Worded differently, the user can apply less force to achieve a fluid tight seal providing more control and mitigating accidental slippage. This is especially important during a wetted environment such as subcutaneous implantation/explantation.

As will be appreciated, impacts, dislocation, or subcutaneous travel of the port 10, catheter 50, may dislodge a locking mechanism causing accidental unlocking or disengagement of the port from the catheter. Advantageously, the securement protrusions 108, 138, and securement apertures 116, 126, 106, prevents accidental unlocking of the mechanism 104. Further, the low profile of the system 100 is compact in a locked position and mitigates dead space that might allow for tissue ingrowth when subcutaneously implanted.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A fluid connector system, comprising:
    a connector body coupled to a catheter body, the connector body configured to engage an access port to place one or more lumens of the access port into fluid communication with one or more lumens of the catheter body; and
    a locking mechanism coupled to the connector body and designed to transition between an unlocked position and a locked position, the locking mechanism comprising:
        a first lever arm rotatably coupled to the connector body; and
        a second lever arm rotatably coupled to the first lever arm, wherein the first lever arm and the second lever arm are oblique to a longitudinal axis of the connector body in the unlocked position, and parallel to the longitudinal axis of the connector body in the locked position, wherein a first end of the second lever arm is releaseably and rotatably coupled to the access port.

2. The fluid connector system according to claim 1, wherein the first lever arm comprises a first securement aperture, and wherein the second lever arm includes a second securement aperture.

3. The fluid connector system according to claim 2, further comprising a securement arm rotatably coupled to the second lever arm, wherein the securement arm includes a protrusion configured to extend through the first securement aperture and the second securement aperture to place the locking mechanism in the locked position.

4. The fluid connector system according to claim 2, wherein the connector body includes a protrusion configured to extend through the first securement aperture and the second securement aperture to place the locking mechanism in the locked position.

5. The fluid connector system according to claim 3, wherein the protrusion engages one of the first securement aperture or the second securement aperture with an interference fit.

6. The fluid connector system according to claim 3, wherein a first end of the securement arm is configured to releasably and rotatably secure the first end of the second lever arm to the access port.

7. The fluid connector system according to claim 3, wherein the access port further includes a socket configured to releasably and rotatably secure one of the first end of the second lever arm or the first end of the securement arm.

8. The fluid connector system according to claim 7, wherein the socket includes an interference fit.

9. The fluid connector system according to claim 8, wherein a first end of the first lever arm, coupled to the connector body, is disposed along the longitudinal axis, between the first end and a second end of the second lever arm in the locked position.

10. A method of fluidly connecting an access port with a catheter, comprising:
providing a connector body coupled to the catheter, the connector body including
a locking mechanism comprising:
a first lever arm rotatably coupled to the connector body; and
a second lever arm rotatably coupled to the first lever arm;
coupling a first end of the second lever arm to the access port; and
transitioning the first lever arm from an unlocked position to a locked position, wherein the first lever arm and the second lever arm are oblique to a longitudinal axis of the connector body in the unlocked position, and parallel to the longitudinal axis of the connector body in the locked position.

11. The method according to claim 10, wherein the connector body is configured to engage the access port to place one or more lumens of the access port into fluid communication with one or more lumens of the catheter.

12. The method according to claim 10, further comprising extending a protrusion through a first securement aperture disposed on the first lever arm and a second securement aperture disposed on the second lever arm to place the locking mechanism in the locked position.

13. The method according to claim 12, further comprising a securement arm rotatably coupled to the second lever arm, and wherein the protrusion extends laterally inward from the securement arm.

14. The method according to claim 12, wherein the protrusion is disposed on the connector body and the protrusion extends laterally outward.

15. The method according to claim 14, wherein the protrusion engages one of the first securement aperture or the second securement aperture with an interference fit.

16. The method according to claim 10, wherein the first end of the second lever arm is releaseably and rotatably coupled to the access port with an interference fit.

17. The method according to claim 13, wherein a first end of the securement arm is configured to releasably and rotatably couple the first end of the second lever arm to the access port.

18. The method according to claim 10, wherein the access port further includes a socket configured to releasably and rotatably couple the first end of the second lever arm to the access port.

19. The method according to claim 10, wherein transitioning the first lever arm from the unlocked position to the locked position further includes disposing a first end of the first lever arm, coupled to the connector body, along the longitudinal axis between the first end and a second end of the second lever arm.

20. A fluid connector system, comprising:
a connector body; and
a locking mechanism coupled to the connector body and designed to transition between an unlocked position and a locked position, the locking mechanism comprising:
a first lever arm rotatably coupled to the connector body, wherein the first lever arm comprises a first securement aperture;
a second lever arm rotatably coupled to the first lever arm, wherein the second lever arm includes a second securement aperture, and wherein the first lever arm and the second lever arm are oblique to a longitudinal axis of the connector body in the unlocked position, and parallel to the longitudinal axis of the connector body in the locked position; and
a securement arm rotatably coupled to the second lever arm, wherein the securement arm includes a protrusion configured to extend through the first securement aperture and the second securement aperture to place the locking mechanism in the locked position.

* * * * *